Figure 1:
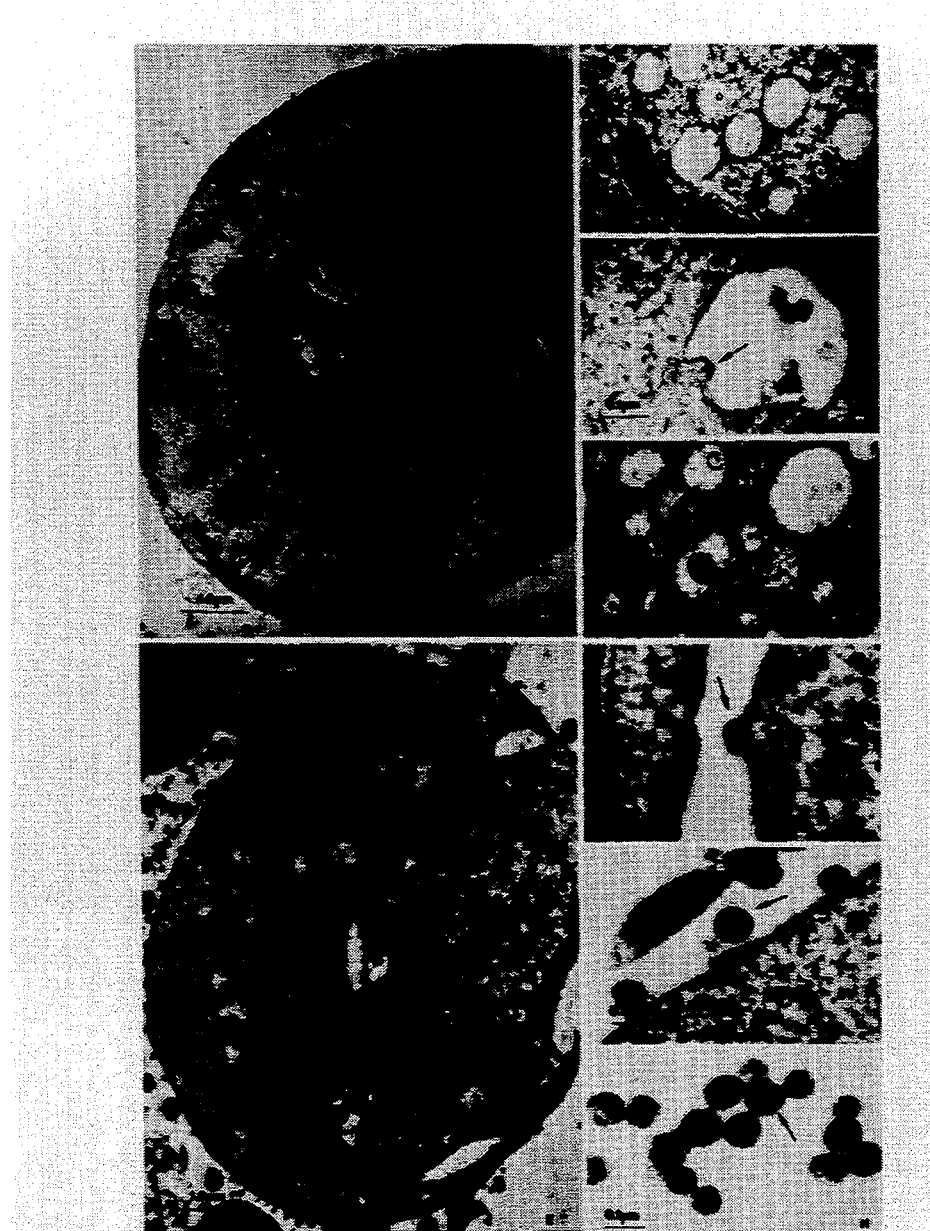

United States Patent [19]

Garry, Jr. et al.

[11] Patent Number: 5,344,774
[45] Date of Patent: Sep. 6, 1994

[54] HUMAN INTRACISTERNAL A-TYPE RETROVIRAL PARTICLES ASSOCIATED WITH SJOGREN'S SYNDROME

[75] Inventors: Robert F. Garry, Jr., New Orleans; Cesar D. Fermin, Mandeville, both of La.; Steve S. Alexander, Jr., Gaithersburg, Md.

[73] Assignee: The Administrators of the Tulane Educational Fund, New Orleans, La.

[21] Appl. No.: 21,180

[22] Filed: Feb. 23, 1993

Related U.S. Application Data

[63] Continuation of Ser. No. 526,349, May 21, 1990, abandoned.

[51] Int. Cl.$^5$ .................. C12N 7/02; C12N 5/08; C12N 7/00; C12N 5/00
[52] U.S. Cl. ..................................... 435/239; 435/5; 435/235.1; 435/240.1; 435/240.2; 930/221
[58] Field of Search ................ 435/235.1, 240.2, 239, 435/240.1

[56] References Cited

PUBLICATIONS

Yang and Wivel, 1973, J. Virol. 11(2):287–298.
The Merck Index, 11th ed., 1989, p. 490, entry 3092.
The Merck Index, 11th ed., 1989, p. 1597, entry 10023.
Garry et al., 1990, Science 250:1127–1129.
Talal et al., 1990, Faseb J. 4:(7)A2102, Abstract No. 2369.
Talal et al., 1990, Arthritis and Rheumatism 33:774–781.
Etkin et al., 1989, ACta Virol. 33:151–161.
Kam–Hansen et al., 1989, Acta Neurol. Scand. 80:467–471.
Ascher et al., 1988, Clin. Exp. Immunol. 73:165–167.
Rucheton et al., 1987, Biol. of the Cell 60:71–72.
Query et al., 1987, Cell 51:211–220.
Leiter et al., 1986, J. Exp. Med. 163:87–100.
Ziegler et al., 1986, Clin. Immunol. Immunopath. 41:305–313.
Ono et al., 1986, in Abstracts of 14th International Cancer Congress, Budapest, Hungary Aug. 12–27, vol. 2, p. 626, Abstract No. 2394.
Maeda et al., 1985, Clin. Exp. Immunol. 60:645–653.
Ono et al., 1985, Keio J. Med. 34:1–16.
Rucheton et al., 1985, Virology 144:468–480.
Barré–Sinoussi et al., 1983, Science 220:868–871.
Belkin et al., 1982, J. Rheumatol. 9:613–616.
Datta et al., 1982, J. Immunol. 129(4):1539–1544.
Kelley et al., 1981, Clin. Immunol. Immunopath. 21:190–203.
Suni et al., 1981, Int. J. Cancer 28:559–566.
Hart et al., 1979, Annals of the Rheumatic Diseases 38:514–525.
Lueders et al., 1979, J. Virol. 30:225–231.
Datta et al., 1978, J. Exp. Med. 147:854–871.
Datta et al., 1978, J. Exp. Med. 147:872–881.
Oldstone et al., 1976, J. Virology 18(1):176–181.
Talal et al., 1974, Curr. Topics Microbiol. Immunol. 6:79–103.

Primary Examiner—Jacqueline Stone
Assistant Examiner—Johnny F. Railey, II
Attorney, Agent, or Firm—Pennie & Edmonds

[57] ABSTRACT

The present invention relates to purified preparations of a novel retrovirus, to methods of diagnosis and treatment of Sjogren's syndrome, novel cell lines, and model systems for the study of autoimmune diseases and AIDS. It is based, in part, on the discovery of a novel retrovirus which is antigenically similar to human immunodeficiency virus but which appears to comprise a functionally distinct reverse transcriptase.

According to the present invention, Sjogren's syndrome as well as other autoimmune diseases, may be diagnosed, and their clinical course may be monitored, by demonstrating the presence of anti-retroviral antibodies and/or measuring the levels of such antibodies. Alternatively, Sjogren's syndrome or other autoimmune diseases may be diagnosed or monitored by directly or indirectly demonstrating vital particles in the cells of a patient.

Furthermore, according to the invention, Sjogren's patients who have been found to exhibit retrovirus or anti-retroviral antibodies may be treated with agents known to be useful in the treatment of retroviral diseases, including but not limited to, agents which interfere with reverse transcriptase function, such as, for example, nucleoside analogues (e.g. zidovudine or dideoxyinosine).

7 Claims, 4 Drawing Sheets

HUMAN INTRACISTERNAL A-TYPE RETROVIRAL PARTICLES ASSOCIATED WITH SJOGREN'S SYNDROME

This is a continuation of application Ser. No. 07/526,349, filed May 21, 1990, now abandoned.

1. INTRODUCTION

The present invention relates to the discovery of a novel retroviral particle associated with Sjogren's syndrome, an autoimmune disease. New methods of diagnosis and treatment of Sjogren's syndrome, novel cell lines comprising the new retrovirus, and model systems for the study of autoimmune diseases and acquired immunodeficiency syndrome (A.I.D.S.) are provided by the present invention.

2. BACKGROUND OF THE INVENTION

The Role of Retroviruses in Autoimmune Disease

Retroviral etiology for several human autoimmune diseases has been proposed, and is the subject of some controversy (Pincus, 1982, Arthritus Rheum. 25:847–856; Norval, 1979, Annals of the Rheumatic Diseases 38:507–513; Hart et al., 1979, Annals of the Rheumatic Diseases 38:514–525; Deman et al., 1976, Transplantation Reviews 31:79–115; Talal, 1978, in "Autoimmunity: Genetic, Immunologic, Virologic and Clinical Aspects," Academic Press, London). It has been demonstrated that self-reactive antibodies in autoimmune diseases, called autoantibodies, may react with components of retroviruses. For example, Rucheton et al. (1987, Biology of the Cell 60:71–72) reports that human autoantibodies reactive with the p30 gag protein of a mouse retrovirus also react with HnRNP, a human ribonucleoprotein molecule.

Often experiments linking retroviruses with particular autoimmune diseases have failed to produce consistent results. For example, Phillips et al. (1978, Annals of the Rheumatic Diseases 35:422–428) reported isolating a retrovirus from the placenta of a systemic lupus erythematosus (SLE) patient, after previously being unable to do so (Phillips et al., 1976, Annals of the Rheumatic Diseases 35:422–428). Further, particles resembling retroviruses have been observed in placentas of SLE patients at a higher frequency than normal placentas (Imamura et al., 1976, Am. J. Pathol. 83:383–394) but interestingly, have not been observed in organs typically involved by SLE (e.g. spleen and kidney).

The literature indicates that a number of researchers are exploring the role of retroviruses in autoimmune disease. For example, Oho et al. (1985, Keio Journal of Medicine 34:1–16), reasoning that the thymus gland is frequently involved in autoimmune disease, cultured thymus cells of autoimmune patients (mainly afflicted with myasthenia gravis, ulcerative colitis, or pure red cell aplasia) with B cells and observed the appearance of retrovirus particles in the cultured thymus cells. Suni et al. (1981, Int. J. Cancer 28:559–566) observed that an antigen related to a retrovital p30 antigen was expressed in highly differentiated syncytiotrophoblasts in human placenta, and suggested that retrovirus-reactive antibodies may represent an autoimmune-like immune response to p30 related antigen which may have escaped during cellular damage (see also Maeda, 1985, Clin. Exp. Immunol. 60:645–653), Kam-Hansen et al. (1989, Acta Neurol. Scand. 80:467–471) has suggested a role for retroviruses in multiple sclerosis. Leiter et al. (1986, J. Exp. Med. 163:87–100) describes a mouse animal model system for diabetes and suggests that retrovital proteins, normally sequestered within pancreatic beta cells, may be expressed on the cell surface as a result of high serum glucose, resulting in autoimmune elimination of glucose-stressed beta cells.

Interestingly, AIDS has been hypothesized to be, at least in part, an autoimmune disease directed at the immune system and triggered by a lymphotrophic retrovirus (Ziegler and Stites, 1986, Clin. Immunol. Immunopathol. 41:305–313). Ziegler and Stites (ibid) have suggested that HIV antigens expressed on the lymphocyte surface may mimic MHC antigens, provoking an autoimmune attack on MHC-bearing cells. Ascher and Sheppard (1988, Clin. Exp. Immunol. 73:165–167) propose that latency of AIDS is not due to delayed viral expression and growth but rather to the accumulation of insults to an immune system with abnormal regulatory mechanisms induced by HIV infection of macrophages.

2.2 Similarities Between Human Immunodeficiency Virus Infection and Sjogren's Syndrome Sjogren's Syndrome (SS; autoimmune exocrinopathy) is among several autoimmune diseases that share clinical symptoms with the diseases induced by human immunodeficiency virus (HIV). Morris et al., 1982, Ann. Intern. Med. 96:714–717; Walsh et al., 1984, New Eng. J. Med. 311:635–639; Stricker et al., 1985, New Eng. J. Med. 313:1375–1380; Dalakas et al., 1986, J.A.M.A. 256:2381–2383; Duvic et al., 1987, J. Am. Acad. Dematol. 17: 656–662 Winchester et al., 1987, Ann. Inter. Med. 106: 19–26; deClerk et al., 1988, Arthritis and Rheumatism 31:272–275; Berman et al., 1988, Am. J. Med. 85: 59–64; Calabrese et al., 1989, Arthritis and Rheumatism 32: 1453–1457; Kopelman and Zolla-Pazner, 1988, Am. J. Med. 84 (1) :82–88; Rynes et al., 1988, Am. J. Med. 84: 810–816; Itescu et al., 1989, Lancet pp. 466–468; Schiot et al., 1989, AIDS .3:819–822). Primary SS is principally characterized by dryness of the mouth and eyes (sicca syndrome) which is also a common manifestation of HIV infection (deClerk et al., 1988, Arthritis and Rheumatism 31:272–275; Calabrese et al., 1989, Arthritis and Rheumatism 32: 1453–1457; Itescu et al. 1989, Lancet pp. 466–468; Schiot et al., 1989, AIDS 3: 819–822). The dryness in both SS and HIV infection is due to destruction of the salivary and lacrimal glands which is accompanied by lymphocytic infiltration. The lymphocytes of approximately 70% of SS patients eventually also infiltrate lungs, kidneys and muscles as the disease progresses. As in HIV disease, localized or generalized lymphadenopathy may develop. In 5–10% of primary SS patients, there is a sudden transformation of the illness characterized by severe weight loss which is reminiscent of HIV-induced wasting. SS patients also produce a variety of autoantibodies, as do persons with other autoimmune diseases and AIDS. Previously, we observed that the sera of 30% of primary SS patients (14/47) contained significant levels of antibodies reactive with the major capsid protein of HIV (CA, p24). Fewer than 1% of control subjects produced this level of anti-gag antibodies.

3. SUMMARY OF THE INVENTION

The present invention relates to purified preparations of a novel retrovirus, to methods of diagnosis and treatment of Sjogren's syndrome, novel cell lines, and model systems for the study of autoimmune diseases and AIDS. It is based, in part, on the discovery of a novel retrovirus which is antigenically similar to human immunodeficiency virus but which appears to comprise a functionally distinct reverse transcriptase.

According to the present invention, Sjogren's syndrome, as well as other autoimmune diseases, may be diagnosed, and their clinical course may be monitored, by demonstrating the presence of anti-retroviral antibodies and/or measuring the levels of such antibodies. Alternatively, Sjogren's syndrome or other autoimmune diseases may be diagnosed or monitored by directly or indirectly demonstrating viral particles in the cells of a patient.

Furthermore, according to the invention, Sjogren's patients who have been found to exhibit retrovirus or anti-retroviral antibodies may be treated with agents known to be useful in the treatment of retroviral diseases, including but not limited to, agents which interfere with reverse transcriptase function, such as, for example, nucleoside analogues (e.g. zidovudine or dideoxyinosine).

4. DESCRIPTION OF THE FIGURES

FIG. 1 (Panels A-H). Electron micrographs of intracisternal A-type retrovirus particles in RH9 cells exposed to salivary gland extracts from SS patients. RH9/MSC cells which were positive for reactivity to HIV-related antigens by antigen capture EIA were fixed, embedded and examined by electron microscopy. Panel A: Low power micrograph of RH9/MSC cells showing area of vacuolar concentration and the presence of a particle with the morphology of a typical intracisternal A-type retrovirus (arrow). Budding particles were not observed at the plasma membrane. Panel B: Selected area from another cell demonstrating hIAP at various stages of assembly. Panel C: Higher power micrograph of a budding hIAP (arrow). Panel D: Higher power micrograph of the hIAP in panel A (arrow). Panel E: Lower power micrograph of RH9 cells persistently-infected with the LA1 strain of HIV-1 prepared by same procedures as hIAP-infected cells. Arrows point to a few of the many particles with the morphology of typical lentiviruses at various stages of budding from the plasma membrane. Particles were not observed in cytoplasmic vacuoles. Panel F: Higher power micrograph of a budding HIV-1 particle showing core structure (arrow). Panel G: Higher power micrograph of the immature HIV virion shown at the largest arrow in panel E (arrow). Panel H: HIV-1 virions at various stages of post-budding maturation. Arrow points to mature HIV-1 virion with typical cylindrical core.

Figure 2A:
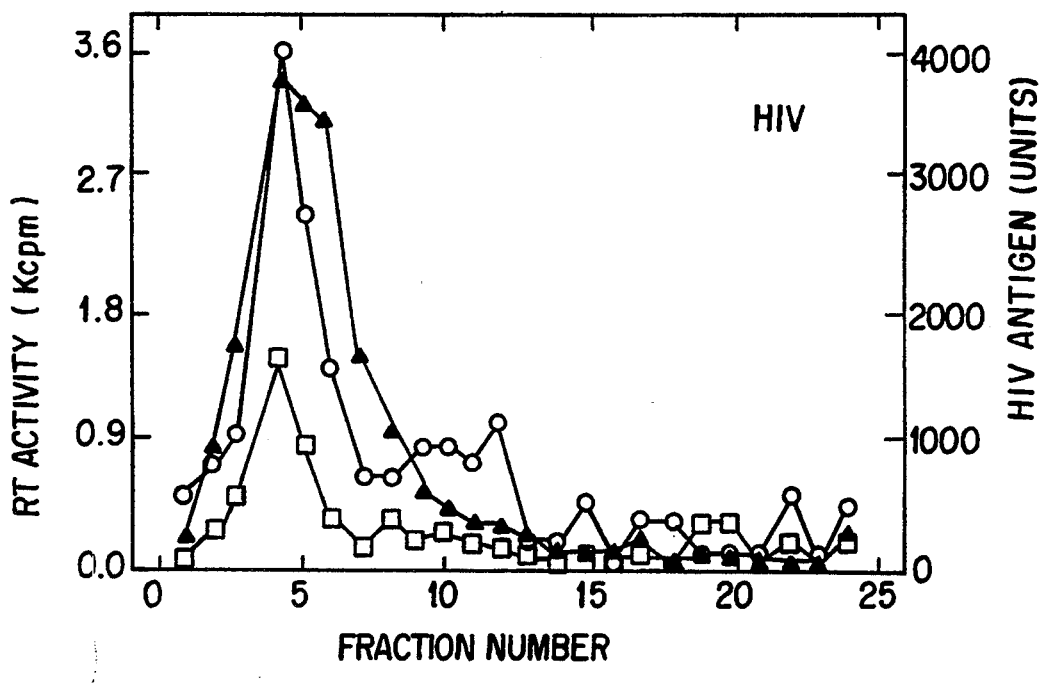
Figure 2B:
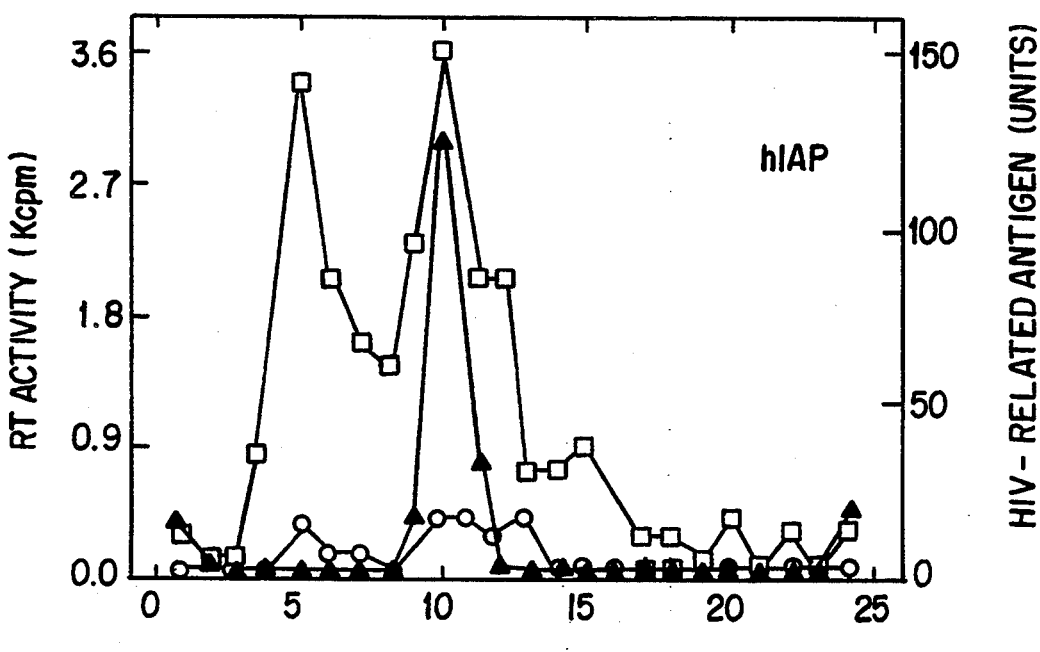

FIG. 2 (Panel A and B). RH9 cells exposed to salivary gland extracts produce particles antigenically-related to HIV with the hydrodynamic properties of an intracisternal A-type particle. Cell lysates from RH9/MSC cells were subjected to procedures previously used for purification of IAP from other species (Yang and Wivel, 1973, J. Virol. 11:287-298) as described in the text. Fractions from the 33 to 68% linear sucrose gradient were tested for the presence of reverse transcriptase activity using $Mn^{++}$ or $Mg^{++}$ as divalent cation, and for the presence of HIV-related antigens by an antigen-capture EIA. Aliquots from each fraction were also tested for refractive index to determine density. A control preparation also subjected to isopycnic banding consisted of concentrated supernatants from RH9 cells persistently-infected with HIV-1 (strain LA1 formerly designated HITI). Other controls are described in the text. Panel A: Gradient centrifugation of HIV-1$_{LA1}$. Panel B: Gradient centrifugation of hIAP. ○—○ Reverse transcriptase activity using $Mg^{++}$ as divalent cation; □—□ reverse transcriptase activity using $Mn^{++}$ as divalent cation; ▲—▲ HIV antigen determined by antigen capture EIA (Abbott).

Figure 3A:
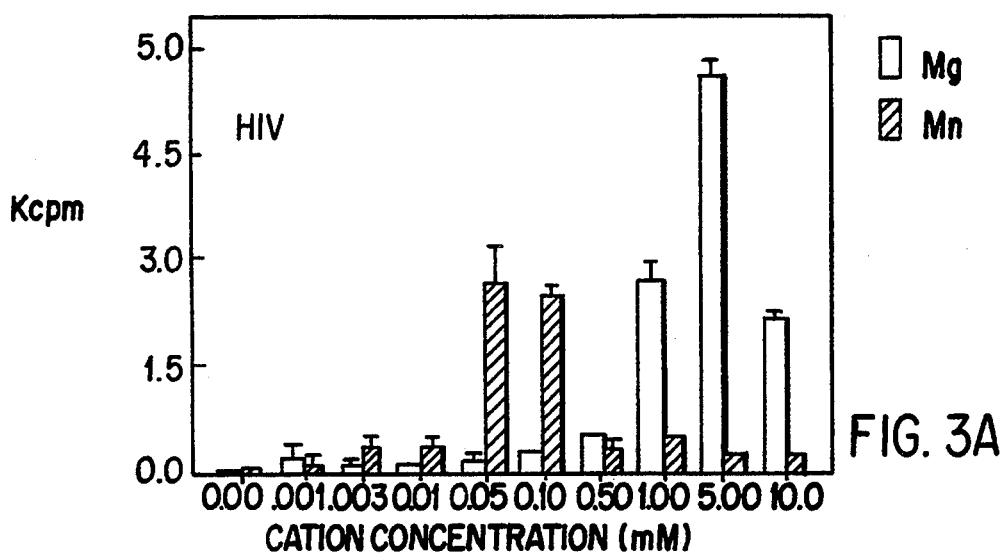
Figure 3B:
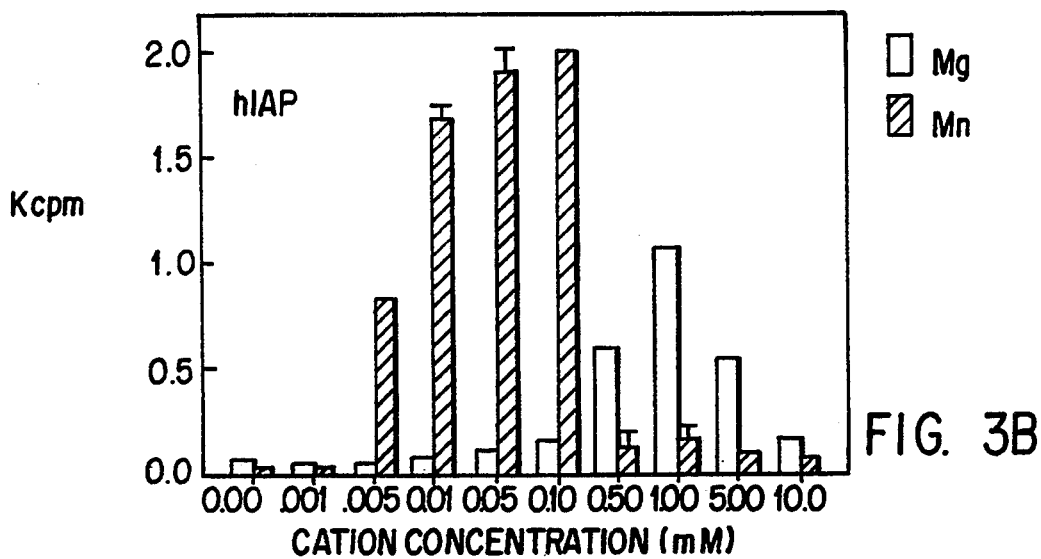
Figure 3C:
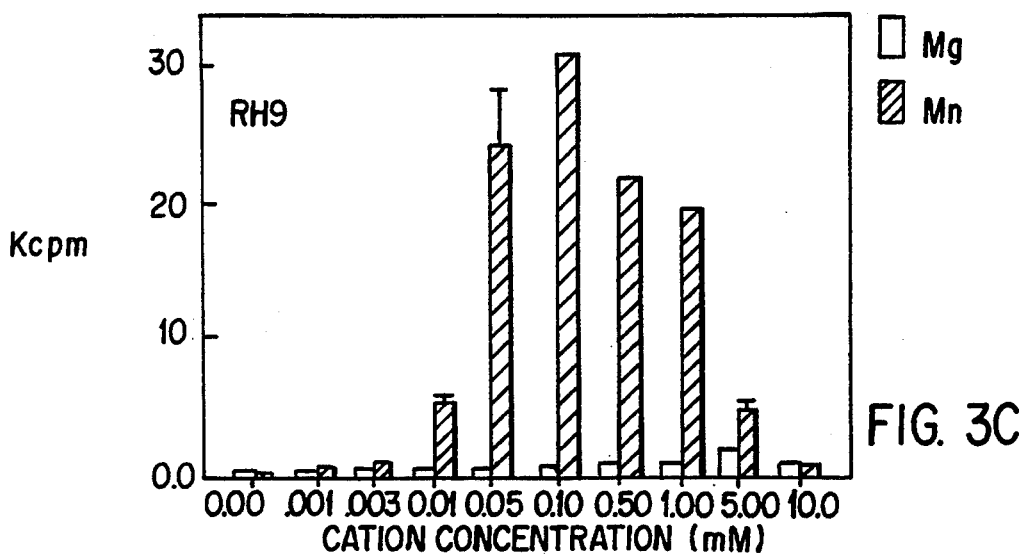

FIG. 3 (Panels A-C). Divalent cation preference of the exogenous reverse transcriptase activities of hIAP, HIV and the polymerase found in uninfected RH9 cells. Standard reverse transcriptase reaction mixtures using polyrA:oligodT as template and primer containing the indicated amount of divalent cation were incubated for 60 minutes and the amount of label from [$^3$H]TTP which became acid precipitate was determined by scintillation counting. White bars represent incorporation using $Mg^{++}$ as divalent cation. Black bars represent incorporation using $Mn^{++}$ as divalent cation.

Figure 4:
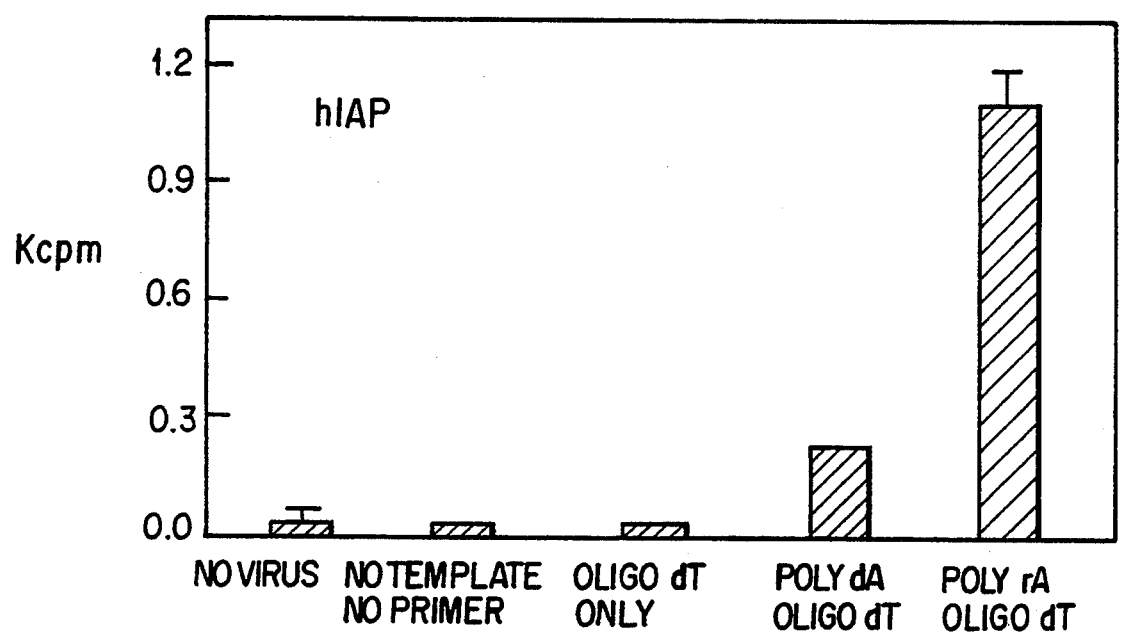

FIG. 4. Template specificities of the hIAP-associated reverse transcriptase. Standard reaction mixtures using various template and primer combinations as indicated were performed in reaction mixtures containing 0.1 mM $Mn^{++}$. The amount of label from [$^3$H]TTP which became acid precipitate after 60 minutes was determined by scintillation counting.

5. DETAILED DESCRIPTION OF THE INVENTION

For purposes of clarity of disclosure, and not by way of limitation, the detailed description of the invention will be divided into the following subsections:
(i) methods of culturing and isolating the Sjogren's Syndrome-associated retrovirus; and
(ii) utility of the invention.

5.1. Methods of Culturing and Isolating the Sjogren's Syndrome-Associated Retrovirus According to the invention, the novel retrovirus described herein may be obtained by culturing lymphoid cells with cells or cell extracts obtained from patients suffering from Sjogren's disease.

Preferably, patient tissues are obtained from areas clinically involved, such as salivary or lacrinal gland. In a preferred embodiment of the invention, lip tissue may be obtained, homogenized (e.g. in a loose fitting tissue grinder in RPMI 1640 medium), and then added to a culture of lymphoid cells, preferably of T lymphocyte lineage. In a specific embodiment of the invention 0.5 g of tissue is homogenized to yield 5 ml of tissue extract, then added to cultures containing $10^7$ cells of the RH9 subclone of HuT 78, a T-lymphoblastic cell line.

Once extracts have been added to the cell cultures, the cell cultures may then be examined from time to time for the presence of retrovirus or retroviral antigen, using standard virological techniques.

For example, cell supernatants or lysates of the cell cultures may be examined by electron microscopy for vital particles. Alternatively, supernatants and lysates may be evaluated by enzyme linked immunosorbent assay (ELISA) techniques utilizing antibody reactive with retrovirus, for example, antibody reactive with HIV (including but not limited to, antibodies reactive with the p24 protein). If retrovirus is present in the cultures, cultures may be expected to screen positive about six to twelve weeks after addition of extracts to cell cultures, although a longer culture period may, in some cases, be necessary. Of note, if cultures are analyzed by electron microscopy, retroviral particles of the invention may be expected to resemble intracisternal A-type particles known in the art (see, for example, Wivel and Smith, 1971, Int. J. Cancer 7:167–175).

Once evidence of the presence of retrovirus in culture has been obtained, virus may be further characterized using methods known in the art to determine its size, molecular biology, etc. For example, and not by way of limitation, cells containing virus may be disrupted in hypotonic buffer, and a microsomal fraction may be prepared. This preparation may then be made about 0.1% in Triton X-100, and then layered over a 48% sucrose cushion. Material which pellets through the cushion may then be applied over a 33–68% (w/v) sucrose gradient and then may be centrifuged at 100,000 g for about 12 hours. Fractions from the sucrose gradient may then be assayed for the presence of retroviral related antigens. The retroviral particles of the invention may be detected in the gradient at a density of about 1.22 g/cm$^3$ or in the range of 1.2 to 1.4 g/cm$^3$. In this manner, a substantially pure preparation of the retrovirus of the invention may be produced.

Furthermore, it may be desirable to ascertain the characteristics of the reverse transcriptase comprised within the retrovirus of the invention. Detergent-disrupted preparations of retrovirus prepared as above may be tested for the ability to synthesize DNA at various concentrations of Mg$^{++}$ and Mn$^{++}$ using polyrA as a synthetic template and oligo dT as primer. According to the invention, the reverse transcriptase of Sjogren's associated retrovirus may be expected to respond more favorably to Mn$^{++}$ rather than Mg$^{++}$ thereby distinguishing it from the reverse transcriptase of HIV, which "prefers" Mg$^{++}$ to Mn$^{++}$.

5.2. Utility of the Invention

5.2.1. METHODS OF DIAGNOSIS

According to the invention, Sjogren's Syndrome may be diagnosed in a patient by screening the patient for the presence of retrovirus or anti-retroviral antibodies. For example, a patient that presents with symptoms and signs consistent with Sjogren's syndrome (e.g. sicca syndrome) may be tested initially for the presence of anti-retrovirus antibodies, including, but not limited to, antibodies reactive with HIV antigens such as p24. Such testing may be performed utilizing any standard technique, including ELISA, in which a patient's serum may be tested for the presence of anti-retroviral antibodies by exposing the serum to immobilized retrovirus or retroviral antigen, and then the binding of antibody to immobilized virus or antigen is detected (e.g. by binding of a second labeled antibody capable of reacting with the antibody adherent to virus or antigen). Alternatively, tissue biopsies, preferably from clinically involved areas, may be tested for the presence of retrovirus or retroviral antigens by in situ hybridization of anti-retroviral antibody to tissue sections or cells using standard techniques or by culturing lymphoid cells in the presence of cell extracts made from the patients cells or tissues, and then detecting the presence of retrovirus in culture according to the methods set forth in Section 5.1. In one specific embodiment of the invention, cells may be scraped from the patients buccal mucosa and then tested for the presence of virus.

At present, antibodies reactive with the retrovirus of the invention also react with HIV. Accordingly, diagnostic tests based on reactivity of a patient's serum with HIV antigen, or which detect retroviral antigen in a patient using anti-HIV antibody do not discriminate between a diagnosis of Sjogren's syndrome and a diagnosis of AIDS. It may or may not be possible to clinically distinguish between the two conditions at various stages of the disease, although in certain cases (e.g. a history of multiple opportunistic infections, Kaposi's sarcoma, etc.) the diagnosis may be more clear. In questionable cases, it may be necessary to culture retrovirus from the patient's tissues, purify said virus using the methods of the invention, and then determine the divalent cation selective properties of the reverse transcriptase present in detergent disrupted viral preparations, in which the reverse transcriptase of the retrovirus of the invention functions optimally in the presence of Mn$^{++}$, whereas HIV reverse transcriptase functions optimally in the presence of Mg$^{++}$ (see Section 5.1., supra).

In further embodiments of the invention the presence of retrovirus or anti-retroviral antibodies may be useful to determine the clinical progression of Sjogren's syndrome, in which case a decline in retrovirus may indicate remission of the disease.

In addition, as shown in Table I, sera from patients suffering from a variety of autoimmune diseases have also been found to be reactive with p24 and/or p17 gag proteins on standard HIV Western blot assays, indicating that additional autoimmune diseases may be associated with the novel retrovirus of the present invention. Accordingly, the present invention provides for the diagnosis of autoimmune diseases via the detection of anti-retroviral antibodies, in particular antibodies reactive with p24 or p17 of HIV. Autoimmune diseases which appear to be most strongly correlated with the production of anti-retroviral antibodies include systemic lupus erythematosus, juvenile rheumatoid arthritis, and scleroderma.

TABLE I

| Antibodies in autoimmune patient sera positive for reactivity to HIV proteins | | |
|---|---|---|
| Diagnosis | Reactive sera/ number tested[a] | Percent Positive |
| Sjogren's Syndrome | 14/47 | 29.8 |
| Systemic lupus erythematosus | 22/61 | 36.1 |
| Scleroderma | 16/55 | 29.1 |
| Juvenile Rheumatoid Arthritis | 7/31 | 22.5 |
| Adult Rheumatoid Arthritis | 3/59 | 5.1 |
| Polymyositis | 1/65 | 1.5 |
| Autoimmune diabetes | 0/20 | 0.0 |
| Hansen's Disease | 0/12 | 0.0 |
| "Normal" Donors | 6/175 | 3.4 |

[a]Sera were positive to p24 and/or p17 gag proteins on standard HIV western blot (Biotech/Dupont).

5.2.2. METHODS OF TREATMENT

As with most autoimmune diseases, the mainstay of therapy for Sjogren's syndrome has been immunosuppressive treatment. The association between a retrovirus and Sjogren's syndrome presents the possibility that anti-retroviral therapy may be effective in treating some, or all patients with the disease. Because it remains unclear whether the presence of retrovirus defines a subgroup of Sjogren's patients, it is recommended that anti-retroviral medication be administered only to those patients with evidence of retrovital infection. Anti-retroviral therapies include but are not limited to compounds which interfere with the function of reverse transcriptase, including nucleoside derivatives such as zidovudine, dideoxyinosine, dideoxydidehydrothymidine, etc.

Because it appears that other autoimmune diseases are associated with retroviral infection (see Table I, supra), such diseases may similarly be treated with anti-retroviral therapies. In particular, the present invention provides for the treatment of systemic lupus erythematosus, juvenile rheumatoid arthritis, and scleroderma by anti-retroviral therapy. 5.2.3. MODEL SYSTEMS FOR THE STUDY OF AUTOIMMUNE DISEASE The substantially purified retrovirus of the invention may be used to generate model systems for autoimmune disease. For example, antibodies directed toward the retrovirus may be induced in laboratory animals which may subsequently be evaluated for autoimmune phenomena. For example, and not by way of 1 imitation, retrovirus containing lymphoid cells generated according to the methods set forth in Section 5.1 may be administered, together with adjuvant, to a primate; standard "booster" doses may subsequently be administered. Animals may then be followed clinically for the appearance of symptoms and signs of autoimmune disease, including the sicca syndrome; tissue biopsies may also be studied.

An important feature of the present invention is that it appears that the retrovirus of the invention is related to HIV, but differs in its cytopathicity. The retrovirus of the invention may provide a method for studying the immunological aberrations caused by HIV which are *not* due to direct cytopathic effects. Further, inactive formulations of the retrovirus of the invention, or antigenic portions thereof, may be useful in the generation of an anti-Sjogren's or, possibly, an anti-HIV vaccine.

6. EXAMPLE: SJOGREN'S SYNDROME: INITIAL CHARACTERIZATION OF A HIV-RELATED INTRACISTERNAL A-TYPE RETROVIRAL PARTICLE PRESENT IN LYMPHOBLASTOID CELLS EXPOSED TO SALIVARY GLAND HOMOGENATES

6.1. Results

SS is diagnosed clinically by histologic examination of the salivary gland for lymphocytic infiltration. Lip tissue contains salivary glands and is the anatomic location of choice for biopsy. Therefore, we attempted to culture an infectious agent from salivary tissue of SS patients. Salivary gland tissues was collected by lip biopsies of six persons with SS. The tissues were then frozen on dry ice, and stored at −70° C. Approximately 0.5 g of tissue was homogenized in a loose-fitting tissue grinder in 5 ml RPMI 1640 medium and 0.5 ml of the crude tissue homogenate was added to cultures containing $10^7$ cells of the RH9 subclone of HuT 78, a T-lymphoblastic cell line. Since a portion of SS patients made antibodies reactive with the gag proteins of HIV we postulated that antibodies reactive to HIV gag proteins might react with a putative retrovirus of SS patients. Therefore, cell-free supernatants and cell lysates were screened in a sensitive and specific antigen capture enzyme-linked immunoassay (Abbott). Uninfected RH9 cells did not produce HIV antigens in cell supernatants or cell lysates detectable in this assay. After 6 weeks, lysates of the cells exposed to one salivary gland biopsy (RH9/MSC) became positive for p24 antigen by an antigen capture EIA (Table II).

TABLE II

Production of HIV-related antigen by RH9 cultures exposed to SS extracts

| Patient | Diagnosis | Time post-exposure (weeks) | | | | | | |
|---------|-----------|---|---|---|---|---|---|---|
|         |           | 2 | 4 | 6 | 8 | 10 | 12 | 16 |
| MSC | SS | − | − | + | + | + | + | + |
| HD  | SS | − | − | − | − | − | + | + |
| DH  | SS | − | − | − | − | − | − | − |
| CR  | SS | − | − | − | − | − | − | − |
| JS  | SS | − | − | − | − | − | − | − |
| FS  | SS | − | − | − | − | − | − | − |
| DC  | normal | − | − | − | − | − | − | − |

However, cell-free supernatants from RH9/MSC cells did not contain significant levels of HIV-related antigens. Lysates of cells exposed to a second biopsy (RH9/HD) became positive for expression of p24 reactivity after 10 weeks in culture. Cultures from four other biopsies from SS patients and one healthy individual remained negative for HIV reactive antigens by EIA for 24 weeks.

To determine if expression of the HIV antigenic reactivity of cells exposed to SS patient salivary gland homogenates was due to production of a viral particle the cells were examined by transmission electron microscopy. HIV, a lentivirus, matures principally at the plasma membrane of infected T-lymphoblastoid cells (Gelderblom et al., 1989, Arch. Virol. 106: 1–3, FIG. 1, panels C-H). Despite the fact that the cells were reacting to HIV antibodies, the RH9/MSC cells failed to produce particles which matured at the plasma membrane. However, evident in some cells in this culture were particles contained within intracytoplasmic vacuoles (FIG. 1, panels A–D). These results are consistent with the absence of HIV-related antigen in culture supernatants. The intracisternal particles consisted of two electron dense concentric rings giving a "doughnut-shaped" appearance. Particles with this distinctive morphology were not found in uninfected RH9 cells or in RH9 cells infected with HIV, despite an extensive search. The particles are morphologically similar to intracisternal A-type particles which have been described in a variety of normal and transformed cells from other species (Wivel and Smith, 1971, Int. J. Cancer 7:167–175.; Calarco and Szollosi, 1973, Nature (New Biology) 243:91–93; Wivel et al., 1973, J. Virol. 11:329–334; Meitz et al., 1987, J. Virol. 61:3020–3029; Kuff and Lueders, 1988, Ad. Cancer Res. 51:184–276). For the purposes of this discussion we will refer to the structures as human intracisternal A-type particles (hIAP).

To physically characterize the particles produced by the RH9/MSC cells, we employed protocols developed for murine A-type retroviruses (Yang and Wivel, 1973, J. Virol. 11:287–298). Cells were disrupted in hypotonic buffer, and a microsomal fraction was prepared. This preparation was made 0.1% in Triton X-100 and layered over a 48% sucrose cushion. Material which pelleted through the cushion was then applied over a 33–68% (w/v) sucrose gradient and centrifuged at 100,000 × g for 12 hours. Similar preparations were made from HIV/RH9 cells and uninfected RH9 cells. In addition, concentrated cell-free supernatants from RH9/MSC, RH9/HIV and uninfected RH9 cells were sedimented in parallel 33–68% sucrose gradients. Fractions of each of the gradients were assayed for the presence of HIV-related antigens by antigen-capture EIA. The major peak of HIV antigen (fractions 4–6) sedimented in this gradient at a density of 1.14–1.16 g/cm$^3$ consistent with previous determinations of the density of HIV (FIG. 2, panel A). This peak is broad because HIV tends to shed the major envelope protein, SU. Additional minor peaks in the gradient correspond to degraded virions or viral antigens associated with subcellular components. RH9/HIV infected cells contain HIV antigenic reactivity dispersed throughout the gradient. RH9/MSC cells did not produce significant levels of HIV-related antigen in the concentrated supernatant fluids, however, a peak of HIV-related antigen from the RH9/MSC cells was detected in the gradient at a density of approximately 1.22 g/cm$^3$ (FIG. 2, panel B, fraction 10). The cellular distribution of the antigenic reactivity is also consistent with the electron microscopic observations. Moreover, this density is similar to that previously determined for A-type particles from other species (Yang and Wivel, 1973, J. Virol. 11:287–298; Robertson et al., 1975, J. Virol. 15:407–415).

One defining characteristic of retroviruses, including A-type retroviruses, is the presence in the vital particle of an RNA-dependent DNA polymerase (reverse transcriptase, RT) (Wilson and Kuff, 1972, PNAS 69:1531–1536; Wong-Staal et al., 1975, J. Virol. 16:887–896; Robertson et al., 1975, J. Virol. 15:407–415). Reverse transcriptases of various retroviruses can often be distinguished on the basis of substrate or ionic preferences (Waite and Allen, 1975, J. Virol. 16:872–879). For example, HIV prefers $Mg^{++}$ over $Mn^{++}$ as a divalent cation when using poly rA as a template and oligo dT as a primer, whereas the reverse preference is shown by the RT of HTLV-I (Rho et al., 1981, Virology 112:355–360); Hoffman et al., 1985, Virology 147:326–335). To determine if the hIAP produced by the RH9/MSC cells contain a reverse transcriptase activity and to define possible distinguishing properties from HIV RT we compared the ability of detergent-disrupted preparations of these viruses to synthesize DNA at various concentrations of $Mg^{++}$ and $Mn^{++}$ using poly rA as a synthetic template and oligo dT as a primer. The optimum concentration for HIV RT activity was 5 mM $Mg^{++}$ whereas the highest activity when $Mn^{++}$ was used was 0.05 mM (FIG. 3, panel A). Under these conditions, the optimum activity using $Mg^{++}$ as divalent cation was 2-fold higher than the highest activity using $Mn^{++}$ as divalent cation. Thus, HIV reverse transcriptase showed a definite preference for $Mg^{++}$ over $Mn^{++}$ as divalent cation in agreement with previously determinations (Hoffman et al., 1985, Virology 147:326–335). In contrast, the highest RT activities associated with hIAP preparations were obtained using $Mn^{++}$ as divalent cation (FIG. 3, panel B). A concentration of 0.1 mM $Mn^{++}$ gave the highest activity which was nearly 2-fold higher than activity at the optimum $Mg^{++}$ concentration (1.0 mM). The results indicate that the RT of the hIAP preparation differs from that of HIV. Fractions of each of the sucrose gradients assayed for the presence of HIV-related antigens were also assayed for $Mg^{++}$- and $Mn^{++}$-dependent RT activities (FIG. 3). The peak of HIV-related antigen from RH9/MSC (1.22 g/cm$^3$) corresponded to a major peak of the $Mn^{++}$-dependent RT activity (FIG. 3, panel B).

Uninfected RH9 cells did not contain HIV-related antigens detectable by this assay in either cell lysates or cell-free supernatants. These cells, however, did contain an endogenous RT activity as is commonly observed in uninfected cells (Nelson et al., 1978, Proc. Natl. Acad. Sci. U.S.A. 75:6263–6267; Sarngadharan et al., 1978, Biochem. Biophys. Acta 516:419–487). This cellular RT could be distinguished from the hIAP-associated RT by sedimentation in a linear sucrose gradient (FIG. 3, panel B, fraction 5 versus fraction 10) and by a greater preference for $Mn^{++}$ over $Mg^{++}$ (over 20-fold compared to 2-fold, FIG. 3, panel C) as well as other cation- and template-preference characteristics.

In additional studies we observed that the hIAP associated RT prefers to utilize RNA (poly rA) over DNA (poly dA) as template (FIG. 4). The hIAP preparation also could not effectively synthesize DNA in a reaction mixture containing only oligo dT. The results of these experiments indicate that the preparation does not contain sufficient levels of a DNA-dependent DNA polymerase nor a deoxyribonucleotidyl (terminal) transferase to account for the observed DNA polymerase activity (Harrison et al. 1976, Biochem. Biophys. Res. Comm. 69:63–67).

In contrast to previous attempts to transfer intracisternal A-type particles from tissues of humans, we were able to induce expression of hIAP in cultured RH9 cells by exposure to salivary gland tissue from a patient with SS. However, attempts to serially transfer the hIAP to uninfected cell lines have to date failed. One explanation for these results is that the A-type particles we observe in the RH9/MSC cells are not infectious, but rather that another type of complete retrovirus particle was present in the salivary tissue of the SS patient. Indeed, it has been suggested that A-type particles are precursors to infectious mouse mammary tumor virus and other retroviruses (Hall et al., 1968, J. Virol. 2:238–247; Kuff and Lueders, 1988, Ad. Cancer Res. 51:184–276; Gelderbaum et al., 1989, Arch. Virol. 106:1–3. It is also possible that a step in the replication of the infectious agent does not occur in the RH9 cell line or that the agent we isolated is replication-defective. In the latter case a helper virus not now present in the hIAP-infected RH9 lines may provide the necessary genetic elements for formation of infectious virus. It is also possible that a component of the patient salivary tissue homogenate induced or selected for stable expression of retroviral sequences present in the genome of RH9 cells a phenomenon previously demonstrated for endogenous retroviruses of other species (Leiter et al., 1986, J. Exp. Med. 163:87–100; Ono et al., 1987, J. Virol. 61:2059–2062; Weist et al., 1989, J. Virol. 63:659–668).

6.2. Discussion

The SS patients participating in the present study were not infected with HIV as determined by confirmatory western blot immunoassay. Furthermore, the retroviral particle isolated by exposure of cultured cells to salivary gland biopsy material, from SS patients could be distinguished from HIV by morphological and physical criteria, and reverse transcriptase divalent cation preference. The isolation of a retroviral particle from cells exposed to salivary gland homogenates of patients with SS raises the possibility that this agent is the antigenic stimulus for the production of HIV gag-reactive antibodies observed in sera from these autoimmune patients (Talal et al., 1990, Arthritis and Rheumatism, in press). However, the studies presented here obviously do not provide proof that the agent we have identified is involved in the etiology of SS or other autoimmune diseases. On the other hand, an association between retrovirus infections and autoimmune phenomena has long been suspected (Levy et al., 1975, J. Virol. 16: 844–853; Imamura et al., 1976, Am. J. Pathol. 83: 383–394; Panem et al., 1976, N. Engl. J. Med. 295: 470–475; Dirksen and Levy, 1977, J. Natl. Cancer Inst. 59: 1187–1192; Rodahl and Iversen, 1985, Ann. Rheum. Dis. 44:761–765; Rucheton et al., 1985, Virology 144:468–480; Query and Keene, 1987, Cell 51:211–220; Kreig et al., 1988, Virology 162: 274–276). A lentivirus has already been demonstrated to induce chronic arthritis in goats (Crawford et al., 1980, Science 207:997–999). An A-type retrovirus of mice has been shown to induce autoimmune diabetes (Leiter et al., 1986, J. Exp. Med. 163:87–100). Interestingly, transgenic mice expressing the tax gene of human T-lymphotropic virus-I have recently been shown to develop exocrinopathy resembling SS (Green et al., 1989, Nature 341:72–74). Other recent studies have linked retrovirus-like nucleic acid sequences to systemic lupus erythematosis and Graves' disease (Hermann et al., 1989, "Molecular and Cellular Mechanisms", New York, Alan R. Liss; Ciampolillo et al., 1989, Lancet, pp. 1096–1100).

7. DEPOSIT OF BIOLOGICAL MATERIALS

The following biological materials were deposited with the American Type Culture Collection (ATCC), Rockville, Md. 20852, USA on Dec. 9, 1992:

RH9/MSC, a cell line comprising HIAP-1, having accession number CRL 11213; and

HIAP-1 viral particles, having accession number VR 2394.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed:

1. A method of preparing a human intracisternal A-type retroviral particle associated with Sjogren's syndrome comprising:
   (i) preparing a homogenized tissue extract from lip tissue taken from a person suffering from Sjogren's syndrome;
   (ii) adding the extract prepared in step (i) to a culture of RH9 cells;
   (iii) culturing the cells exposed to the extract according to step (ii) for a period of about six weeks;
   (iv) lysing the cultured cells and preparing a microsomal fraction therefrom;
   (v) treating the microsomal fraction with detergent;
   (vi) layering the detergent-treated microsomal fraction of step (v) on a 33–68% (w/v) sucrose gradient;
   (vii) centrifuging the sucrose gradient at about 100,000 g for about 12 hours; and
   (viii) collecting the fraction corresponding to a density of about 1.2.

2. A substantially purified human intracisternal A-type retroviral particle prepared by a method, comprising:
   (i) preparing a homogenized tissue from lip tissue taken from a person suffering from Sjogren's syndrome;
   (ii) adding the extract prepared in step (i) to a culture of RH9 cells;
   (iii) culturing the cells exposed to the extract according to step (ii) for a period of about six to ten weeks;
   (iv) lysing the cells and preparing a microsomal fraction therefrom;
   (v) treating the microsomal fraction with detergent;
   (vi) layering the detergent-treated microsomal fraction of step (v) on a 33–68% (w/v) sucrose gradient;
   (vii) centrifuging the sucrose gradient at about 100,000 g for about 12 hours; and
   (viii) collecting the fraction corresponding to a density of about 1.2.

3. The substantially purified human intracisternal A-type retroviral particle of claim 2, which comprises a reverse transcriptase which exhibits greater activity in a solution comprising 0.10 mM manganese ion than in a solution comprising 0.10 mM magnesium ion.

4. A homogenized tissue line produced by adding a cell extract prepared from lip tissue taken from a patient suffering from Sjogren's syndrome to a culture of RH9 cells, such that the cell line produces intracisternal A-type particles comprising a reverse transcriptase which exhibits greater activity in a solution comprising 0.10 mM manganese ion than in a solution comprising 0.10 mM magnesium ion.

5. A cell line comprising the human intracisternal A-type retroviral particle associated with Sjogren's syndrome of claim 1 and having ATCC accession number CRL 11213.

6. A substantially purified human intracisternal A-type retroviral particle derived from RH9/MSC cells having ATCC accession number CRL 11213.

7. The substantially purified human intracisternal A-type retroviral particle of claim 1 having ATCC accession number VR 2394.

* * * * *